(12) United States Patent
Woodruff et al.

(10) Patent No.: US 8,852,118 B2
(45) Date of Patent: Oct. 7, 2014

(54) TELEMETRY DEVICE WITH SOFTWARE USER INPUT FEATURES

(75) Inventors: Scott A. Woodruff, Cincinnati, OH (US); Amy L. Marcotte, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 368 days.

(21) Appl. No.: 12/685,004

(22) Filed: Jan. 11, 2010

(65) Prior Publication Data

US 2011/0172687 A1 Jul. 14, 2011

(51) Int. Cl.
| | |
|---|---|
| *A61B 5/00* | (2006.01) |
| *A61F 2/02* | (2006.01) |
| *A61F 13/00* | (2006.01) |
| *A61F 2/00* | (2006.01) |
| *A61F 5/00* | (2006.01) |

(52) U.S. Cl.
CPC ............. *A61F 5/0059* (2013.01); *A61F 5/0056* (2013.01)
USPC ................................ 600/561; 600/30; 600/37

(58) Field of Classification Search
CPC ........ A61B 17/12; G08C 19/16; G06T 11/20; G06F 3/01; A61F 5/0056; A61F 5/0059
USPC ................................ 600/37, 587, 593; 607/60
See application file for complete search history.

(56) References Cited

U.S. PATENT DOCUMENTS

| | | | |
|---|---|---|---|
| 6,067,991 A | 5/2000 | Forsell | |
| 6,461,292 B1 | 10/2002 | Forsell | |
| 6,470,892 B1 | 10/2002 | Forsell | |
| 7,416,528 B2 | 8/2008 | Crawford et al. | |
| 7,442,165 B2 | 10/2008 | Forsell | |
| 7,601,162 B2 | 10/2009 | Hassler, Jr. et al. | |
| 7,621,863 B2 | 11/2009 | Forsell | |
| 7,699,770 B2 | 4/2010 | Hassler, Jr. et al. | |
| 7,798,954 B2 | 9/2010 | Birk et al. | |
| 2005/0283118 A1 | 12/2005 | Uth et al. | |
| 2006/0199997 A1 | 9/2006 | Hassler, Jr. et al. | |
| 2006/0211914 A1 | 9/2006 | Hassler, Jr. et al. | |
| 2007/0167672 A1 | 7/2007 | Dlugos et al. | |
| 2008/0250340 A1 | 10/2008 | Dlugos, Jr. et al. | |
| 2009/0222065 A1* | 9/2009 | Dlugos et al. ................. 607/60 |

FOREIGN PATENT DOCUMENTS

| | | |
|---|---|---|
| EP | 2 085 058 | 8/2009 |
| EP | 2 095 798 | 9/2009 |

OTHER PUBLICATIONS

International Search Report dated Mar. 24, 2011 for Application No. PCT/US2011/020471.

* cited by examiner

*Primary Examiner* — Brian Szmal
(74) *Attorney, Agent, or Firm* — Frost Brown Todd LLC

(57) ABSTRACT

An implantable restriction device is configured to provide a restriction in a patient. A pressure sensor implanted in the patient is configured to sense pressure associated with the restriction device. A remote input device is configured to wirelessly receive pressure measurements from the pressure sensor and transmit the pressure measurements to a display device. The display device is configured to plot the pressure measurements as a function of time. The remote input device also includes buttons that may be used to annotate the pressure measurements, such as to indicate physical events associated with the patient (e.g., coughing, sneezing, etc.). The display device is also configured to display the annotations on or near the plot of pressure measurements. A viewer may thus take the annotations into account when evaluating the pressure measurements, such as by ignoring pressure measurements associated with certain types of annotations.

20 Claims, 16 Drawing Sheets

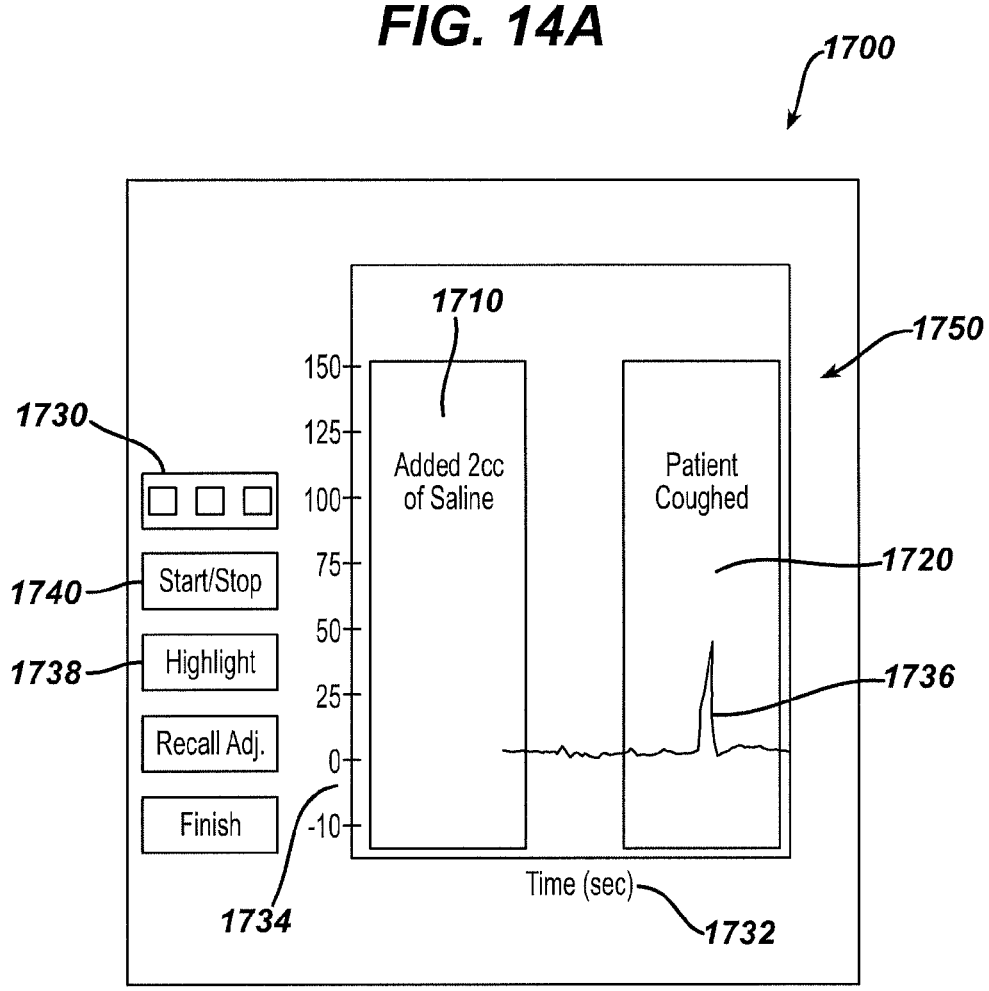

TELEMETRY DEVICE WITH SOFTWARE USER INPUT FEATURES

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of fluid actuated gastric bands are disclosed in U.S. Pat. No. 7,416,528, entitled "Latching Device for Gastric Band," issued Aug. 26, 2008, the disclosure of which is incorporated by reference herein. Another example of such a gastric band is disclosed in U.S. Pat. No. 6,067,991, entitled "Mechanical Food Intake Restriction Device," issued May 30, 2000, the disclosure of which is incorporated by reference herein. Examples of a mechanically actuated gastric band are disclosed in U.S. Pat. No. 7,601,162, entitled "Actuator for an Implantable Band," issued Oct. 13, 2009, the disclosure of which is incorporated by reference herein. Other examples of mechanically actuated gastric bands are described in U.S. Pub. No. 2007/0167672, entitled "Feedback Sensing for a Mechanical Restrictive Device," published Jul. 19, 2007, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 14A shows an exemplary flagging adjustment fluid and patient coughing display for a graphical user interface;

Figure 1:
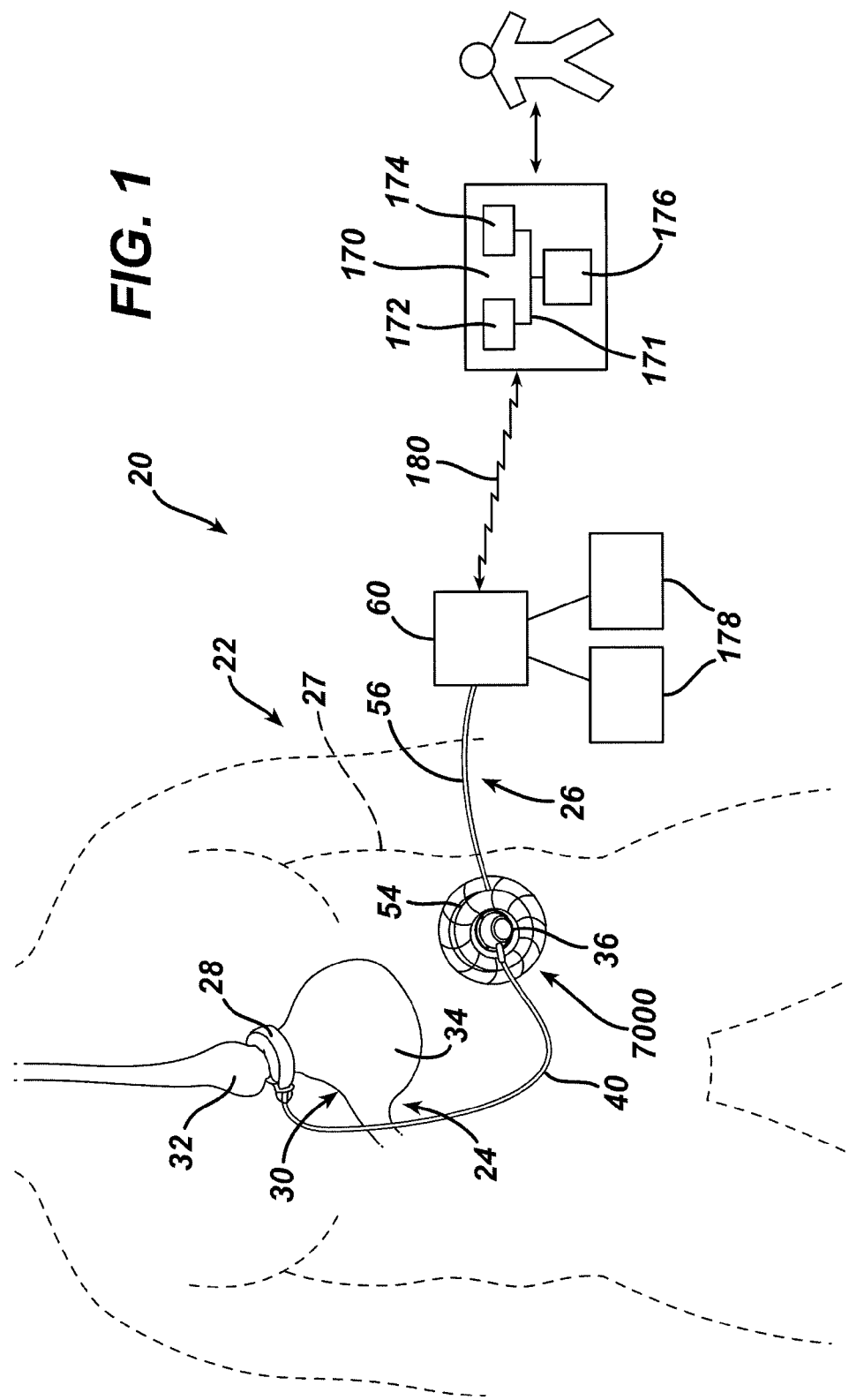
FIG. 1 is a simplified, schematic diagram of an exemplary implanted restrictive opening device and an exemplary bi-directional communication system between the implanted device and a remote monitoring unit.

The drawings are not intended to be limiting in any way, and it is contemplated that various versions of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, versions, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Referring now to the drawings in detail, wherein like numerals indicate the same elements throughout the views, FIG. 1 provides a simplified, schematic diagram of a bi-directional communication system (20) for transmitting data between an implanted restrictive opening device and a remotely located monitoring unit. Through communication system (20), data and command signals may be transmitted between the implanted device and a remotely located physician for monitoring and affecting patient treatment. The communication system of the invention enables a physician to control the restrictive opening device and monitor treatment without meeting face-to-face with the patient. In FIG. 1 and the following disclosure, the restrictive opening device is shown and described as being a food intake restriction device (22) for use in bariatric treatment. The use of a food intake restriction device is only representative however, and the examples described herein may be utilized with other types of implanted restrictive opening devices without departing from the scope of the invention.

As shown in FIG. 1, a first portion (24) of intake restriction device (22) is implanted beneath a patient's skin (27), while a second portion (26) is located external to the patient's skin. Implanted portion (24) comprises an adjustable restriction band (28) that is implanted about the gastrointestinal tract for the treatment of morbid obesity. In this example, adjustable band (28) is looped about the outer wall of a stomach (30) to create a stoma between an upper pouch (32) and a lower pouch (34) of the stomach. Adjustable band (28) may include a cavity defined by a bladder made of silicone rubber, or another type of biocompatible material, that inflates inwardly against stomach (30) when filled with a fluid. Alternatively, band (28) may comprise a mechanically adjustable device having a fluid cavity that experiences pressure changes with band adjustments, or a combination hydraulic/mechanical adjustable band.

An injection port (36), which will be described in greater detail below, is implanted in a body region accessible for needle injections and telemetry communication signals. In the version shown, injection port (36) fluidly communicates with adjustable band (28) via a catheter (40). A surgeon may position and permanently implant injection port (36) inside the body of the patient in order to perform adjustments of the food intake restriction or stoma. Injection port (36) may be implanted in the lateral, subcostal region of the patient's abdomen under the skin and layers of fatty tissue. Alternatively, the surgeon may implant injection port (36) on the sternum of the patient or at any other suitable location.

Figure 2:
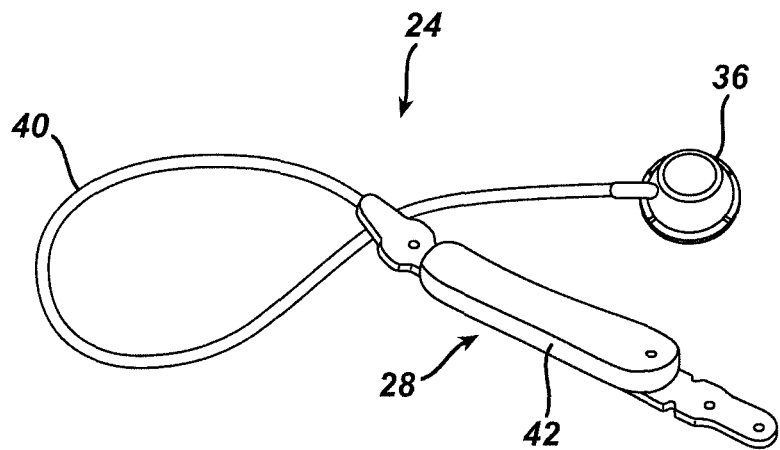
FIG. 2 is a more detailed, perspective view of an implantable portion of the food intake restriction device shown in FIG. 1.

FIG. 2 illustrates adjustable band (28) in greater detail. In this version, band (28) includes a variable volume cavity (42) that expands or contracts against the outer wall of the stomach to form an adjustable stoma for controllably restricting food intake into the stomach. A physician may decrease the size of the stoma opening by adding fluid to variable volume cavity (42) or, alternatively, may increase the stoma size by withdrawing fluid from cavity (42). Fluid may be added or withdrawn by inserting a needle into injection port (36). The fluid may be, but is not restricted to, a 0.9 percent saline solution.

Returning now to FIG. 1, external portion (26) of intake restriction device (22) comprises a hand-held antenna (54) electrically connected in this version via an electrical cable assembly (56) to a local unit (60). Antenna (54) comprises a coil that is enclosed in a remote input device (7000), which will be discussed in more detail below. Electrical cable assembly (56) may be detachably connected to local unit (60) or antenna (54) to facilitate cleaning, maintenance, usage, and storage of external portion (26). In some version, electrical cable assembly (56) is omitted, and antenna (54) is coupled with local unit (60) wirelessly. Local unit (60) of the present example is a microprocessor-controlled device that communicates with implanted device (22). By way of example only, local unit (60) may comprise a conventional desktop computer, a laptop computer, a portable electronic device (e.g., BlackBerry, iPhone, etc.), a customized/dedicated device, or any other suitable type of device, including combinations thereof. In some versions, local unit (60) may also communicate with a remote unit (170), as will be described further below. Through antenna (54), local unit (60) non-invasively communicates with implanted injection port (36). For instance, antenna (54) in remote input device (7000) may be held against the patient's skin (27) near the location of injection port (36) to transmit telemetry and power signals to injection port (36); and to receive telemetry signals from injection port (36).

As is also shown in FIG. 1, communication system (20) of the present example also includes a remote monitoring unit (170) in addition to local unit (60). Remote unit (170) may be located at a physician's office, a hospital or clinic, or elsewhere. Remote unit (170) of the present example is a personal computer type device comprising a microprocessor (172), which may be, for example, an Intel Pentium® microprocessor or the like. Alternatively, remote unit (170) may comprise a dedicated or non-dedicated server that is accessible over a network such as the Internet. In the present example, a system bus (171) interconnects microprocessor (172) with a memory (174) for storing data such as, for example, physiological parameters and patient instructions. A graphical user interface (176) is also interconnected to microprocessor (172) for displaying data and inputting instructions and correspondence to the patient. User interface (176) may comprise a video monitor, a touchscreen, or other display device, as well as a keyboard or stylus for entering information into remote unit (170). Other devices and configurations suitable for providing a remote unit (170) will be apparent to those of ordinary skill in the art in view of the teachings herein.

A number of peripheral devices (178) may interface directly with local unit (60) for inputting physiological data related to the patient's condition. This physiological data may be stored in local unit (60) and uploaded to remote unit (170) during an interrogation or other data exchange. Examples of peripheral devices that can be utilized with the present invention include a weight scale, blood pressure monitor, thermometer, blood glucose monitor, or any other type of device that could be used outside of a physician's office to provide input regarding the current physiological condition of the patient. A weight scale, for example, can electrically communicate with local unit (60) either directly, or wirelessly through antenna (54), to generate a weight loss record for the patient. The weight loss record can be stored in memory (138) of local unit (60). During a subsequent interrogation by remote unit (170), or automatically at prescheduled intervals, the weight loss record can be uploaded by microprocessor (136) to remote unit (170). The weight loss record may be stored in memory (174) of remote unit (170) until accessed by the physician.

Also as shown in FIG. 1, a communication link (180) is created between local unit (60) and remote unit (170) for transmitting data, including voice, video, instructional information and command signals, between the units. Communication link (180) may comprise any of a broad range of data transmission media including web-based systems utilizing high-speed cable or dial-up connections, public telephone lines, wireless RF networks, satellite, T1 lines or any other type of communication medium suitable for transmitting data between remote locations. Of course, as with other components described herein, remote unit (170) is merely optional, and remote unit (170) may be omitted entirely if desired. In versions where a remote unit (170) is included, communication system (20) may further include a data logger and associated components as described in U.S. Pub. No. 2006/

0199997, entitled "Monitoring of a Food Intake Restriction Device," published Sep. 7, 2006, the disclosure of which is incorporated by reference herein.

Figure 3:
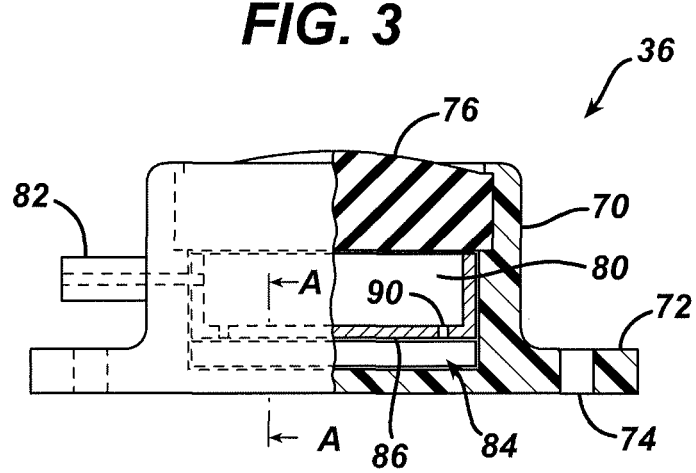
FIG. 3 is a side, partially sectioned view of the injection port shown in FIG. 2.

FIG. 3 depicts a side, partially sectioned view of an exemplary injection port (36). As shown in FIG. 3, injection port (36) comprises a rigid housing (70) having an annular flange (72) containing a plurality of attachment holes (74) for fastening the injection port to tissue in a patient. A surgeon may attach injection port (36) to the tissue, such as the fascia covering an abdominal muscle, using any one of numerous surgical fasteners including suture filaments, staples, and clips. In some versions, injection port (36) has integral fasteners that are selectively extendable to secure injection port (36) within the patient. For instance, injection port (36) may be configured in accordance with at least some of the teachings of U.S. Pub. No. 2005/0283118, entitled "Implantable Medical Device with Simultaneous Attachment Mechanism and Method," published Dec. 22, 2005, the disclosure of which is incorporated by reference herein. Alternatively, injection port (36) may have any other suitable configuration and/or operability.

Injection port (36) of the present example further comprises a septum (76). Septum (76) may be made of a silicone rubber and compressively retained in housing (70). Alternatively, septum (76) may be formed of any other suitable material(s) and/or may be retained in housing (70) in any other suitable fashion. Septum (76) is penetrable by a Huber needle, or a similar type of injection instrument, for adding or withdrawing fluid from port (36). Septum (76) self-seals upon withdrawal of the syringe needle to maintain the volume of fluid inside of injection port (36). Injection port (36) further comprises a reservoir (80) for retaining the fluid (e.g., saline) and a catheter connector (82). Connector (82) attaches to catheter (40), shown in FIG. 2, to form a closed hydraulic circuit between reservoir (80) and cavity (42) within adjustable band (28). Housing (70) and connector (82) may be integrally molded from a biocompatible polymer or constructed from a metal such as titanium or stainless steel. Of course, various other configurations and versions for a port (36) will be apparent to those of ordinary skill in the art in view of the teachings herein.

Injection port (36) of the present example also comprises a pressure sensor (84) for measuring the pressure of fluid within reservoir (80). The pressure measured by sensor (84) may correspond to the amount of restriction applied by band (28) to the patient's stomach (30) or other body cavity. Accordingly, measuring the fluid pressure may enable a physician to evaluate the restriction caused by band (28), as well as the results of adjustments to band (28) to change the restriction. The pressure measurement may be transmitted from sensor (84) to local unit (60) via telemetry signals using antenna (54). Local unit (60) may process, display, print, and/or transmit the pressure measurement to a remote monitoring unit for evaluation, as will be described in more detail below. In the version shown in FIG. 3, pressure sensor (84) is positioned at the bottom of fluid reservoir (80) within housing (70). A retaining cover (86) extends above pressure sensor (84) to substantially separate the sensor surface from reservoir (80), and protect the sensor from needle penetration. Retaining cover (86) may be made of a ceramic material such as, for example, alumina, which resists needle penetration yet does not interfere with electronic communications between pressure sensor (84) and antenna (54). Retaining cover (86) includes a vent (90) that allows fluid inside of reservoir (80) to flow to and impact upon the surface of pressure sensor (84).

Figure 4:
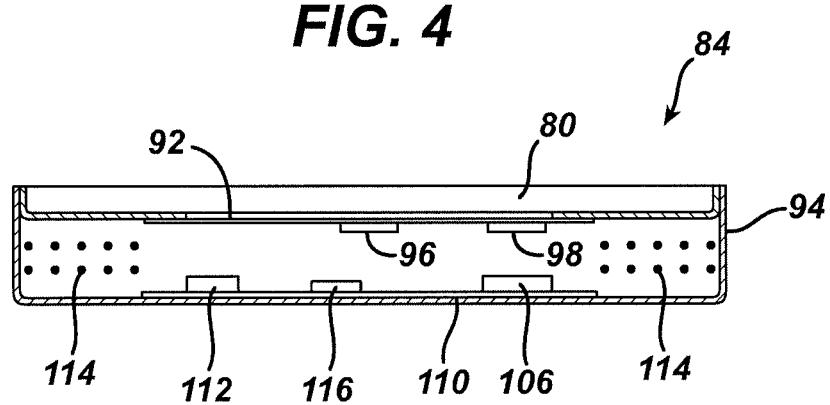
FIG. 4 is a side, sectional view, taken along line A-A of FIG. 3, illustrating an exemplary pressure sensor for measuring fluid pressure in the intake restriction device of FIG. 2.

FIG. 4 is a side, sectional view of pressure sensor (84), taken along line A-A of FIG. 3, illustrating a version for measuring fluid pressure. Pressure sensor (84) is hermetically sealed within a housing (94) to prevent fluid infiltrating and effecting the operation of sensor (84). The exterior of pressure sensor (84) includes a diaphragm (92) having a deformable surface. In some versions, diaphragm (92) is formed by thinning out a section of the bottom of titanium reservoir (80) to a thickness between 0.001" and 0.002". As fluid flows through vent (90) in reservoir (80), the fluid impacts upon the surface of diaphragm (92), causing the surface to mechanically displace. The mechanical displacement of diaphragm (92) is converted to an electrical signal by a pair of variable resistance, silicon strain gauges (96, 98). Strain gauges (96, 98) are attached to diaphragm (92) on the side opposite the working fluid in reservoir (80). Strain gauge (96) is attached to a center portion of diaphragm (92) to measure the displacement of the diaphragm. The second, matched strain gauge (98) is attached near the outer edge of diaphragm (92). Strain gauges (96, 98) may be attached to diaphragm (92) by adhesives, or may be diffused into the diaphragm structure. As fluid pressure within band (28) fluctuates, the surface of diaphragm (92) deforms up or down at the bottom of reservoir (80). The deformation of diaphragm (92) produces a resistance change in the center strain gauge (96).

Figure 5:
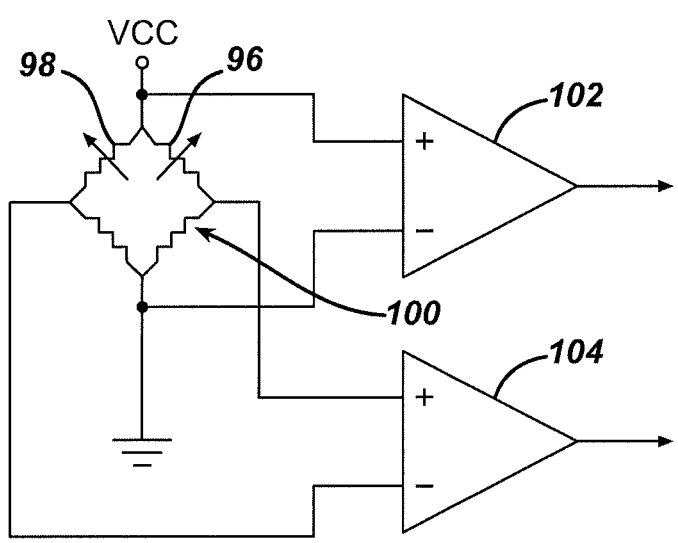
FIG. 5 is a simplified schematic of an exemplary variable resistance circuit for the pressure sensor shown in FIG. 4.

As shown in FIG. 5, strain gauges (96, 98) form the top two resistance elements of a half-compensated, Wheatstone bridge circuit (100). As strain gauge (96) reacts to the mechanical displacements of diaphragm (92), the changing resistance of the gauge changes the potential across the top portion of the bridge circuit. Strain gauge (98) is matched to strain gauge (96) and athermalizes the Wheatstone bridge circuit. Differential amplifiers (102, 104) are connected to bridge circuit (100) to measure the change in potential within the bridge circuit due to the variable resistance strain gauges. In particular, differential amplifier (102) measures the voltage across the entire bridge circuit, while differential amplifier (104) measures the differential voltage across the strain gauge half of bridge circuit (100). The greater the differential between the strain gauge voltages, for a fixed voltage across the bridge, the greater the pressure difference. If desired, a fully compensated Wheatstone bridge circuit could also be used to increase the sensitivity and accuracy of the pressure sensor (84). In a fully compensated bridge circuit, four strain gauges are attached to the surface of diaphragm (92), rather than only two strain gauges as shown in FIG. 4.

Returning to FIG. 4, the output signals from differential amplifiers (102, 104) are applied to a microcontroller (106). Microcontroller (106) is integrated into a circuit board (110) within housing (94). A temperature sensor (112) measures the temperature within injection port (36) and inputs a temperature signal to microcontroller (106). Microcontroller (106) uses the temperature signal from sensor (112) to compensate for variations in body temperature and residual temperature errors not accounted for by strain gauge (98). Compensating the pressure measurement signal for variations in body temperature may increase the accuracy of the pressure sensor (84). Additionally, a TET/telemetry coil (114) is located within housing (94). Coil (114) is connected to a capacitor (116) to form a tuned tank circuit for receiving power from and transmitting physiological data, including the measured fluid pressure, to local unit (60). FIGS. 3-5 illustrate just one merely exemplary version for measuring fluid pressure within an intake restriction device. Of course, a pressure sensing system in injection port (36) (and/or elsewhere within implanted portion (24)) may have a variety of other components and configurations. By way of example only, the above described pressure sensing components may be substituted or supplemented with any of the various types of pressure sensing components described in U.S. Pub. No. 2006/0211914, entitled "System and Method for Determining Implanted Device Positioning and Obtaining Pressure Data" published Sep. 21, 2006, the disclosure of which is incorporated by reference herein. Still other suitable components and configurations for an implantable pressure sensing system will be apparent to those of ordinary skill in the art in view of the teachings herein.

Figure 6:
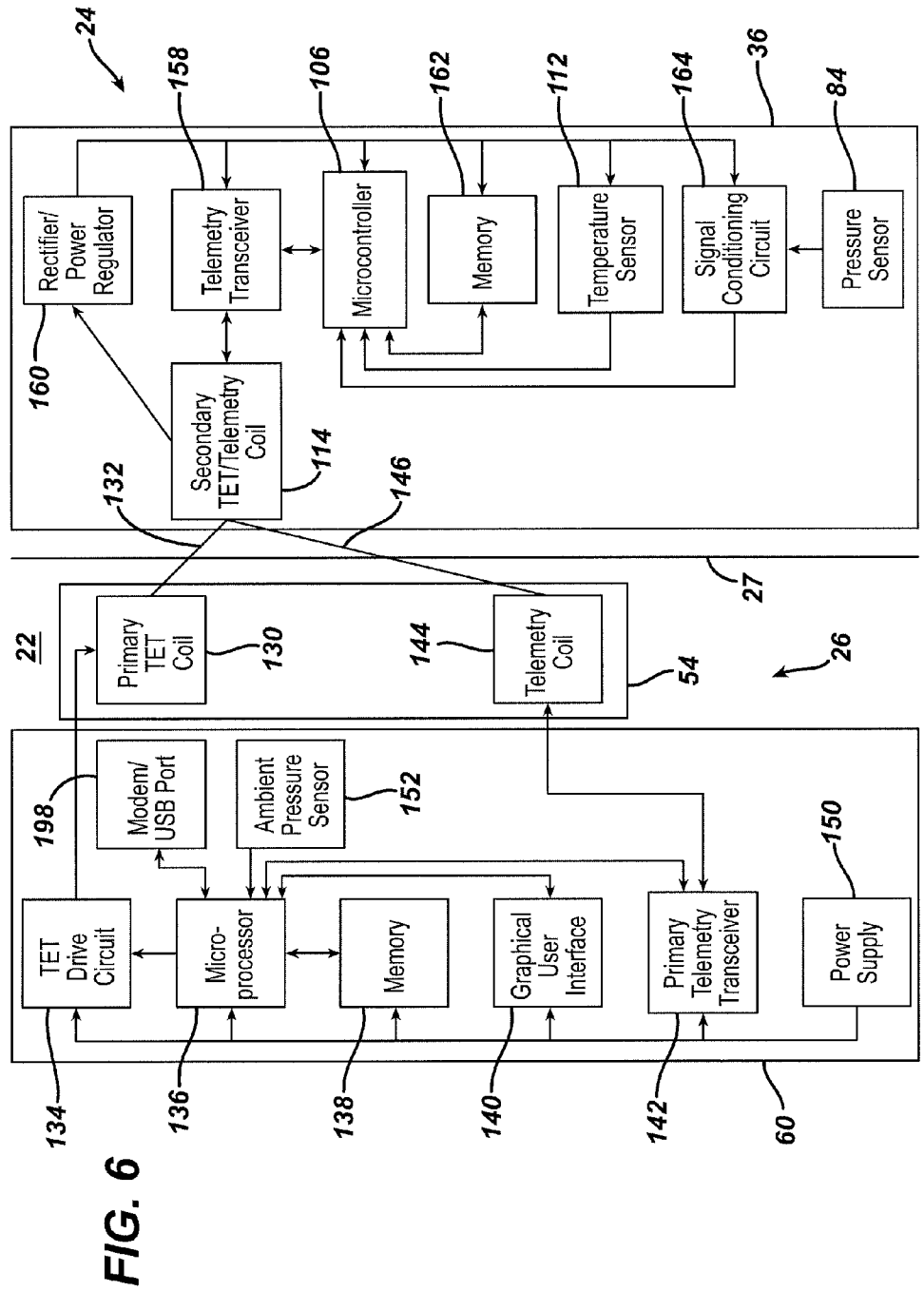
FIG. 6 is a block diagram of exemplary internal and external components of the intake restriction device shown in FIG. 1.

FIG. 6 also illustrates some exemplary components of implanted portion (24) of device (22). As shown in FIG. 6, secondary TET/telemetry coil (114) receives power and communication signals from external antenna (54). Coil (114) forms a tuned tank circuit that is inductively coupled either with primary TET coil (130) to power the implant, or with primary telemetry coil (144) to receive and transmit data. Of course, coils (130, 144) may be consolidated into a single coil that provides both TET and telemetry functionality, if desired. A telemetry transceiver (158) controls data exchange with coil (114). Additionally, implanted portion (24) includes a rectifier/power regulator (160), microcontroller (106) described above, a memory (162) associated with the microcontroller, temperature sensor (112), pressure sensor (84) and a signal conditioning circuit (164) for amplifying the signal from pressure sensor (84). The implanted components transmit the temperature adjusted pressure measurement from sensor (84) to local unit (60) via TET/telemetry coil (114), with local unit (60) receiving the transmitted signals via antenna (54). The pressure measurement may be stored in memory (138) within local unit (60), shown on a display within local unit (60), or transmitted in real time to a remote monitoring station (e.g., remote unit (170) shown in FIG. 1).

Figure 7:
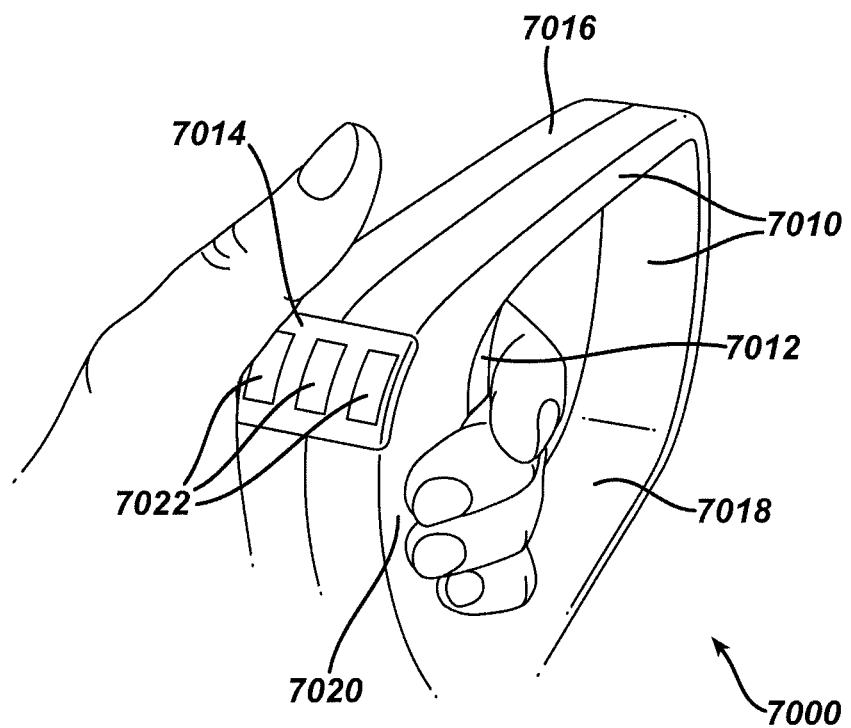
FIG. 7 is a perspective view of an exemplary remote input device.
Figure 8:
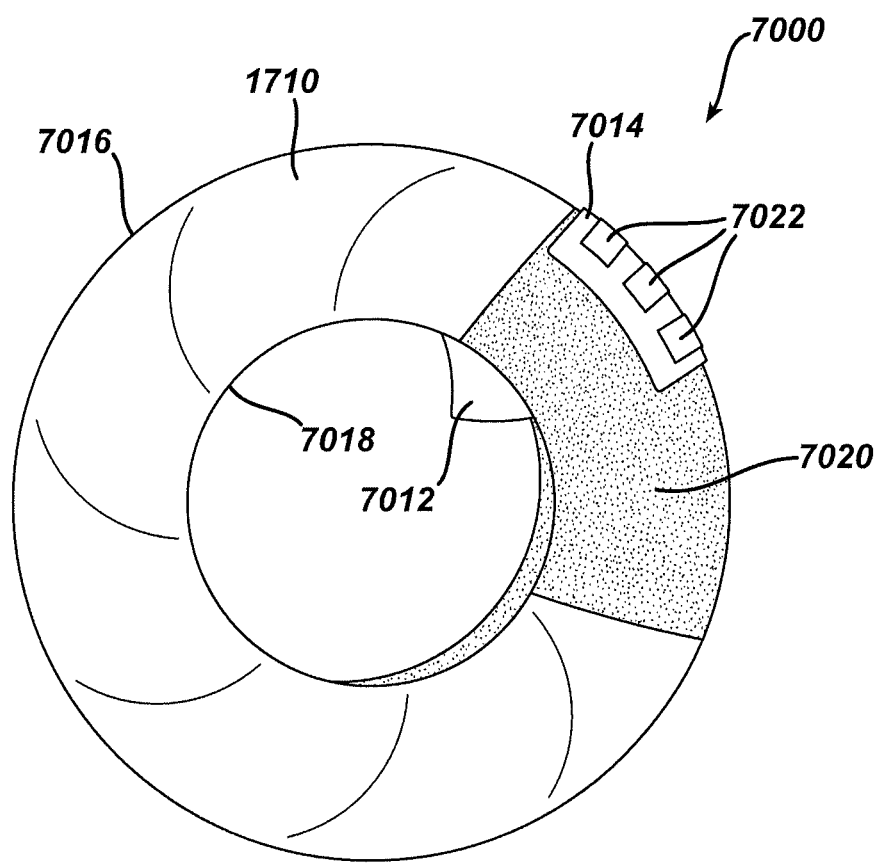
FIG. 8 is a side view of the remote input device of FIG. 7.

FIGS. 7-8 show an exemplary remote input device (7000). Remote input device (7000) comprises a remote housing (7010), antenna (54), and an input interface (7014). Remote input device (7000) may also include various other components of external portion (26) shown in FIG. 6. In addition, remote input device (7000) may be coupled with local unit (60) via cable assembly (56) and/or wirelessly. It should also be understood that components of external portion (26) shown in FIG. 6 may be essentially split between remote input device (7000) and local unit (60). For instance, remote input device (7000) may comprise antenna (54), TET drive circuit (134), primary telemetry transceiver (142), and ambient pressure sensor (152); while local unit (60) may include microprocessor (136), memory (138), graphical user interface (140), and modem/USB port (198). Power supply (150) may be provided by a battery in local unit (60), a battery in remote input device (7000), an external source (e.g., wall outlet), etc. Various other suitable ways in which components of external portion (26) shown in FIG. 6 may be allocated among local unit (60) and remote input device (7000) will be apparent to those of ordinary skill in the art in view of the teachings herein. Similarly, other various components that may be added to (or omitted from) local unit (60) and/or remote input device (7000) will be apparent to those of ordinary skill in the art in view of the teachings herein.

Remote housing (7010) of the present example is generally round or toroidal in shape and comprises an outer surface (7016) corresponding generally to the outer circumference of toroidal shape of remote input device (7000) and an inner surface (7018) defined by the inner circumference of toroidal shape of remote input device (7000). Inner surface (7018) defines an opening whereby a user's hand may be inserted to grasp remote input device (7000). Remote input device (7000) may be other shapes as well including, but not limited to rectangular, ovular, elliptical, or spheroidal. In addition, in the present example, the opening defined by inner surface (7018) permits a user to insert a needle and/or other components of a syringe through the opening, such as to penetrate septum (76) of injection port (36) to add or withdraw fluid from reservoir (80) to adjust the degree of restriction created by adjustable band (28). A user may thus adjust the degree of restriction created by adjustable band (28) with a needle inserted through the central opening of remote input device (7000) while also simultaneously holding remote input device (7000) near the patient to obtain pressure data and while also simultaneously manipulating buttons (7022) to annotate the pressure data and/or provide other inputs, etc., as will be described in greater detail below. Gripping portion (7020) of the present example is contoured and textured to allow the user to easily grip remote input device (7000). Gripping portion (7020) may be constructed of a rubber or other elastomeric/non-slip material.

Figure 9:
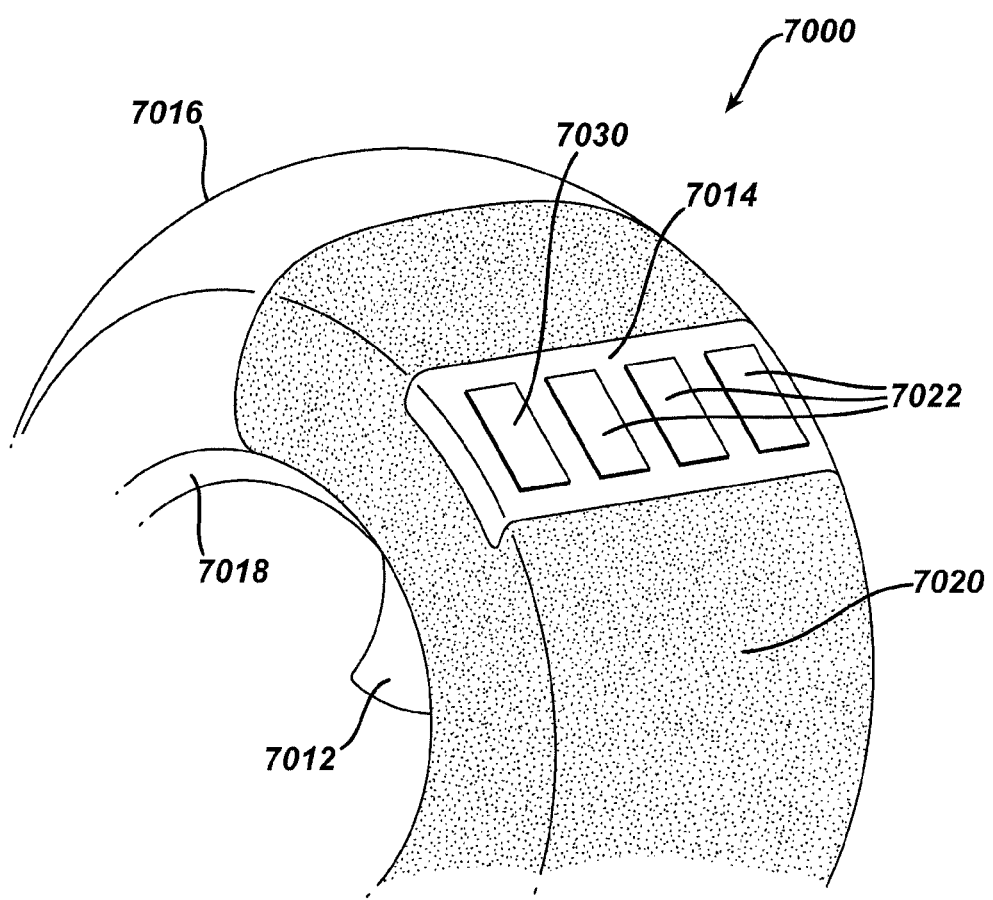
FIG. 9 is an enlarged partial view of the remote input device of FIG. 7, showing a user interface of the remote input device.

As shown in FIG. 9, input interface (7014) comprises a plurality of buttons (7022) that may be pressed, manipulated, or otherwise engaged. Buttons (7022) may comprise conventional electromechanical buttons, thin film switches, capacitive switches, or any other suitable type(s) of devices, components, or structures. Alternatively, input interface (7014) may comprise a dial, touchscreen, keyboard, levers, knobs, switches, sliders, or any other interface that a physician or other users can engage to produce or otherwise trigger an input signal. Input interface (7014) is located on outer surface (7016) of remote housing (7010) near gripping portion (7020) so as to allow the user to engage input interface (7014) with the user's thumb while holding remote input device (7000). Operation of input interface involves pressing a selected one of plurality of buttons (7022), but may also be configured to accept other inputs including, but not limited to, a voice command or a gesture by the user. Thus, for example, a user can press a button (7022), whereby the press of a button translates into a signal to be sent to microprocessor (7024), as will be described in more detail below.

Remote input device (7000) further comprises a trigger (7012). In the version depicted, remote input device (7000) comprises a single trigger (7012), but remote input device (7000) may comprise a plurality of triggers (not shown). Trigger (7012) is located on inner surface (7018) of remote input device (7000). Trigger (7012) is located such that a physician or other user may engage trigger (7012) while grasping remote input device (7000). Trigger (7012) may further comprise a lock (not shown) which is configured to hold down trigger (7012), such that a user may engage lock (not shown) to temporarily hold down trigger (7012) without requiring additional force. Trigger (7012) may be any shape that allows the user to engage trigger (7012) while grasping gripping portion (7020) such as, but not limited to a trigger-like shape, a button (not shown), a sliding member, a lever, etc., or any other variation that will be apparent to one of ordinary skill in the art based on the description herein. It should also be understood that trigger (7012) or plurality of triggers (not shown) may be located on any portion of remote input device (7000). For instance, each of plurality of triggers (not shown) may be positioned at different locations such that each of plurality of triggers (not shown) may be engaged simultaneously with different hands of the user grasping different portions of remote housing (7010).

Remote input device (7000) of the present example is constructed of a rigid material. Rigid material may comprise a plastic, fiber glass, ceramic, titanium, rubber, or other materials operable to avoid interfering with signals being transmitted and received by antenna (54). As noted above, input interface (7014) comprises a plurality of buttons (7022), which may also constructed of a rigid material such as, but not limited to plastic, fiber glass, ceramic, titanium, or rubber. Similarly, trigger (7012) may be constructed of a rigid material including, but not limited to plastic, rubber, or other materials. Trigger (7012) and/or input interface (7014) may be a contrasting color with housing to increase visibility of trigger (7012) and/or input interface (7014).

Figure 10:
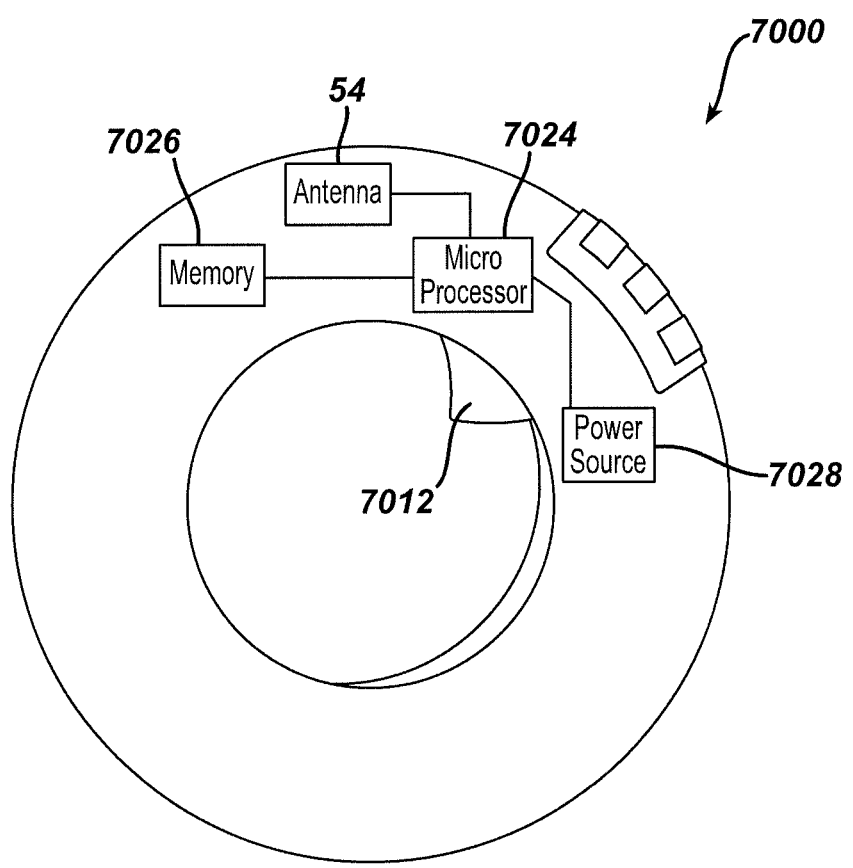
FIG. 10 is a schematic diagram illustrating interior components of the remote input device of FIG. 7.

Turning now to FIG. 10, enclosed in remote housing (7010) of the present example is antenna (54), a microprocessor (7024), a memory (7026), and a power source (7028). Antenna (54) comprises a coil located circumferentially around the inside of remote housing (7010). Microprocessor (7024) is in communication with input interface (7014). Microprocessor (7024) is also in communication with antenna (54). Microprocessor (7024) may be, for example, an Intel Pentium® microprocessor or the like. In the present example, microprocessor (7024) is in communication with memory (7026) for storing data such as, for example, programmed instructions for associating each of plurality of buttons (7022) with an event.

Upon pressing one of plurality of buttons (7022) or engaging trigger (7012), a sensor (not shown) translates the input into a signal communicated to microprocessor (7024), which communicates the signal to local unit (60) via electrical cable assembly (56). Alternatively, transmitter (not shown) may be configured to transmit signals to local unit (60) wirelessly via telemetry signals or in any other suitable fashion.

Microprocessor (7024) may be powered by a rechargeable cell (not shown), such as a rechargeable battery. In some versions, the rechargeable cell is removable and may be recharged using a recharging unit and replaced with another rechargeable cell while the spent cell is recharging. In some other versions, the rechargeable cell is recharged by plugging a recharging adapter into remote input device (7000) and a wall unit. In some other versions, the rechargeable cell is recharged wirelessly by a wireless recharging unit. Alternatively, microprocessor (7024) may be powered by power signals communicated from local unit (60) via electrical cable assembly (56), or by any other suitable source.

Returning now to FIG. 9, input interface (7014) comprising plurality of buttons (7022) is programmed to send a variety of signals to local unit (60) by way of microprocessor (7024) and communicated via electrical cable assembly (56). It will be appreciated that over the course of an office visit or longer term, it may be helpful to notate physical occurrences that may affect measurements in intraband pressure data to explain or suggest what might otherwise be seen as abnormalities or false readings regarding the intraband pressure. Each button (7022) is programmed to transmit a signal to local unit (60) corresponding to a physical event including, but not limited to eating, drinking, adding or removing fluid to and from the band, coughing, talking, laughing, hiccupping, lying down, sitting up, standing up, burping, sneezing, vomiting, dry swallowing, or other event. Furthermore, a single button (7030) may be programmed to note that a button was mistakenly pressed. Each of plurality of buttons (7022) may be individually programmed or preprogrammed. For instance, each button (7022) may be programmed to correspond with a particular physical event, such that the user may select a particular button (7022) to indicate the occurrence of a particular event.

As patient experiences any of the physical events, the user presses a button (7022) that corresponds to the physical event, which sends a signal associated with the physical event to local unit (60). As described in greater detail below, the signals associated with pressing of buttons (7022) may be used to time stamp, annotate, or otherwise correlate with pressure data associated with the same time period at which the physical event occurred. Each of plurality of buttons (7022) may be pressed multiple times, thereby sending multiple signals corresponding to multiple physical events. It should also be understood that physical events may be designated into event groups, and each particular button (7022) may be associated with a corresponding particular event group. For instance, a first event group may include coughing, hiccupping, burping, sneezing, and vomiting. A second event group may include eating, drinking, or dry swallowing. A third event group may include the patient moving from a supine position to a sitting position, the patient moving from a sitting position to a standing position, etc. A fourth event group may include the physician adding fluid to band (28) and the patient withdrawing fluid from the band (28). Each of these event groups may have their own associated button (7022), such that the user can activate the appropriate button (7022) when an event occurs in that button's associated event group.

An additional button (7030) may be included to effectively "cancel" a previous button (7022) activation, or to otherwise send a signal indicating that a previous activation of a button (7022) was inadvertent. In other words, in the event that a button (7022) is inadvertently pressed, single button (7030) programmed to note that a button (7022) was mistakenly pressed may be used to note that a button (7022) was inadvertently pressed.

Additionally, it will be appreciated that the physician or user may wish, without placing remote input device (7000) down, to start and stop recording readings related to intraband pressure data as they are transmitted to antenna (54) and thus to local unit (60). Trigger (7012) is configured to generate a start signal and a stop signal whereby start and stop signal begins and ends recording of intraband pressure data, respectively. Thus, upon engaging trigger (7012), remote input device (7000) communicates a signal to local unit (60) to begin recording and/or displaying intraband pressure data. Upon releasing trigger (7012), or alternatively, engaging trigger (7012) a second time, remote input device (7000) communicates a signal to local unit (60) to stop recording and/or displaying intraband pressure data.

Figure 11:
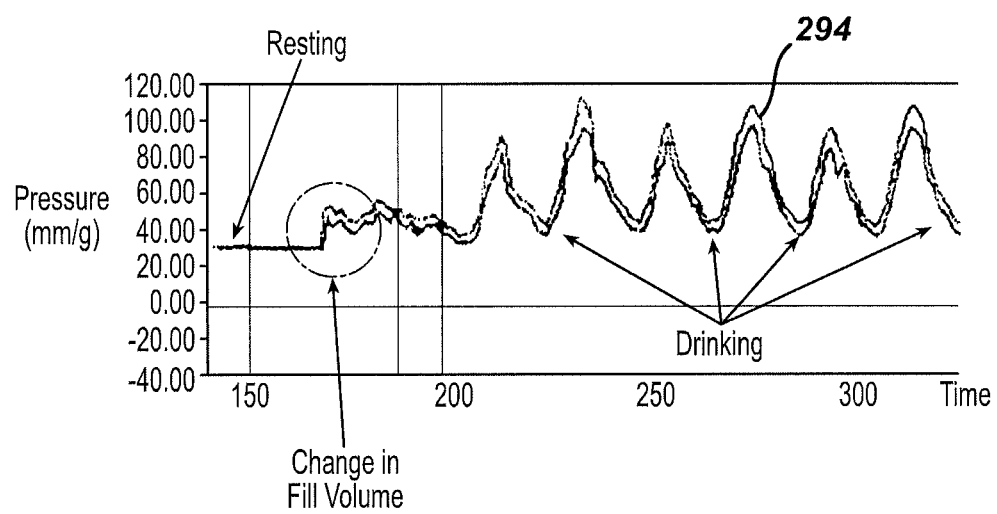
FIG. 11 is a graphical representation of a fluid pressure measurement from the sensor shown in FIG. 4, as communicated through the system of the present invention.
Figure 12:
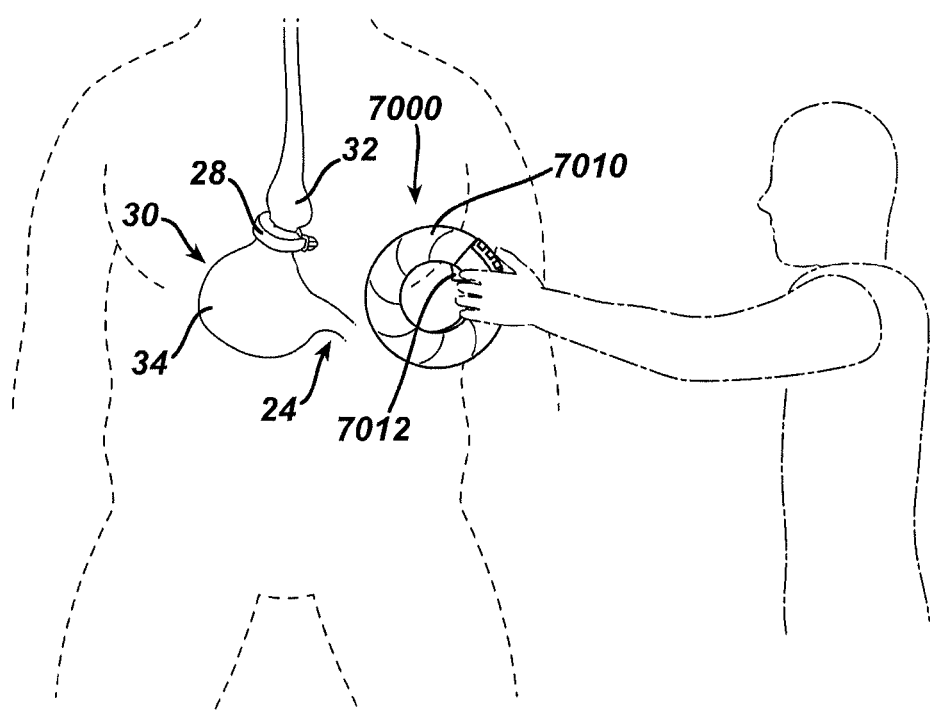
FIG. 12 depicts a physician using remote input device in bi-directional communication with implanted device.

FIG. 11 is a graphical representation of an exemplary pressure signal (294) as measured by sensor (84) during repeated interrogation by remote input device (7000) and local unit (60) over a sampling time period. Pressure signal (294) may be displayed using graphical user interface (140) of local unit (60) and/or graphical user interface (176) of remote unit (170). Pressure signal (294) may also form at least part of a pressure measurement log, which may be generated during the course of an office visit. In particular, remote input device (7000) is configured for use with a patient locally with local unit (60). As shown in FIG. 12, a physician may hold remote input device (7000) near patient, near adjustable band (28) in patient. That is, the physician may hold remote input device (7000) directly in front of the patient at about the location where adjustable band (28) is located. However, in some versions, remote input device (7000) may still properly function regardless of the orientation of remote input device (7000) in relation to the patient. Further, remote input device (7000) may be used with the patient regardless of whether the patient is sitting, standing, or lying down.

In the example shown in FIGS. 11-12, the fluid pressure in band (28) is initially measured while the patient is stable, resulting in a steady pressure reading as shown. Next, an adjustment is applied to band (28) to decrease the stoma size. In particular, the needle of a syringe is percutaneously inserted into septum (76), and a plunger of the syringe is actuated to add fluid to band (28) via injection port (36). During the band adjustment, pressure sensor (84) continues to measure the fluid pressure and transmit the pressure readings through the patient's skin to local unit (60). In particular, pressure readings from pressure sensor (84) are communicated transcutaneously from coil (114) in injection port (36) to antenna (54) in remote input device (7000), which further transmits the pressure readings to local unit (60) via cable assembly (56). In some versions, particularly when antenna (54) comprises an annular coil, the coil of antenna (54) is substantially coaxially aligned with coil (114) in injection port (36) during such communication. In some other versions, the coil of antenna (54) is axially offset relative to coil (114) in injection port (36) during such communication. Alternatively, other suitable configurations and/or relationships may be used. As seen in the graph of FIG. 11, fluid pressure rises following the band adjustment.

In the example shown, the patient is asked to drink a liquid after the adjustment to check the accuracy of the adjustment. As the patient drinks, pressure sensor (84) continues to measure the pressure spikes due to the peristaltic pressure of swallowing the liquid. The physician may evaluate these pressure spikes (either locally or from a remote location) in order to evaluate and direct the patient's treatment. If the graph indicates pressure spikes exceeding desired levels, the physician may immediately take corrective action (either locally or through communication system (20), and view the results of the corrective action, until the desired results are achieved. Accordingly, a physician can perform an adjustment and visually see the results of the adjustment.

During a pressure reading session, if an event inadvertently affects the pressure measurement received by antenna (54), the physician can press one of plurality of buttons (7022) to send a signal to local unit (60), whereby an annotation regarding the corresponding pressure data is noted. If, for example, the patient sneezes while the local unit (60) records pressure measurements, the sneeze may create pressure data information that may mischaracterize the data to someone who later observes the pressure data information without knowledge or recollection of the patient's sneeze. Thus, the physician can instead press a button (7022) on remote input device (7000) programmed to correspond to patient sneezing, which then communicates a signal to local unit (60) to annotate the pressure data with a note indicating that the patient sneezed at the moment in time corresponding with the contemporaneous pressure data. The physician is thus able to annotate the pressure data without putting down remote input device (7000) or otherwise having to approach local unit (60) to note the occurrence of the sneeze.

Figure 13A:
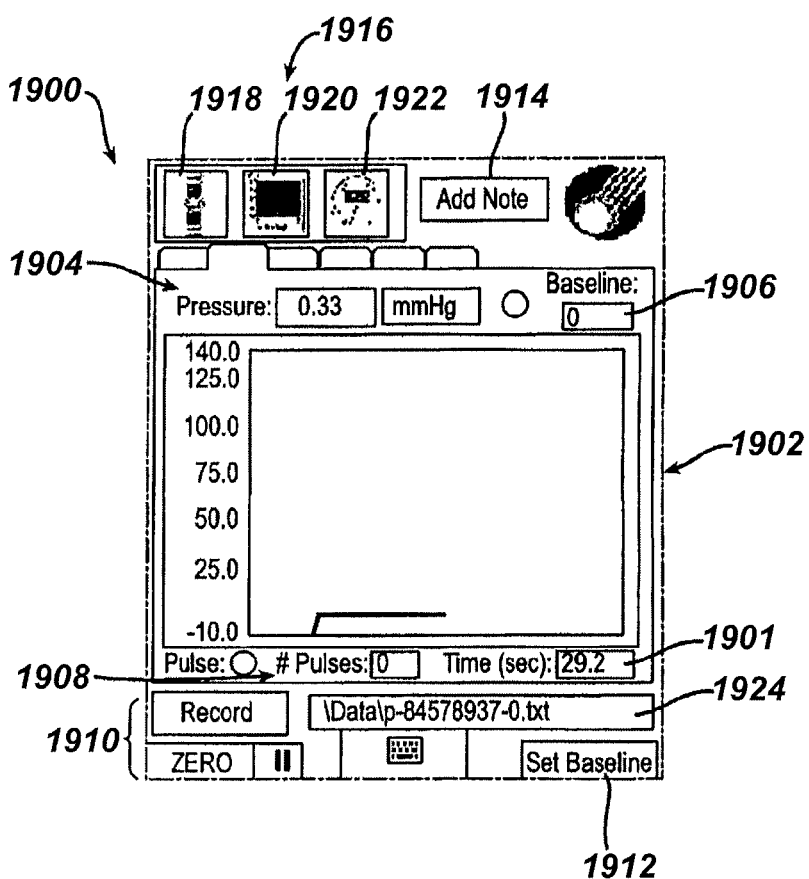
FIG. 13A shows an exemplary pressure graph display for a graphical user interface.

The graphical user interface of local unit (60), remote monitoring unit (170), or another external or physiological monitoring device in the communication system (20), can provide a wide variety of displays based on or related to data or information from the restriction device (22). The displays can include information about measurements taken by the restriction device (22), such as the measurements of the fluid pressure sensed within a fluid-fillable restriction device, pressure in a mechanically-adjustable restriction device, or other parameters (e.g., pulse widths, pulse durations, pulse amplitude, pulse count or pulse frequency, sensed electrical characteristics, etc.), or about physiological events, conditions (e.g., of the restriction device (22), such as its restricted or fill state), or trends. FIG. 13A, for example, shows one exemplary version of a display (1900) that can be used as part of a graphical user interface (e.g., graphical user interface (140) of local unit (60), etc.).

As shown in FIG. 13A, display (1900) includes a plot or graph (1902) of pressure over time, which is shown as a line graph but could also be a bar graph, scatter graph, or virtually any other graphic representation. The time scale along the horizontal axis (1901) can be automatically sized to the amount of pressure data available or can be user-adjustable, e.g., to examine a time period of interest. The display (1900) can also include a textual indicator (1904), which as shown numerically provides a current or instantaneous pressure reading. A wide variety of other kinds of information also can be presented on display (1900), including a baseline indicator (1906) showing a steady-state or baseline value of the pressure and pulse indicators (1908) showing the number of pulses (for example, the pulses may be pressure pulses which can represent or be caused by the peristaltic contractions of a patient swallowing). In some versions, this information can be obtained through user input (via the "Set Baseline" button (1912) or by entering visually detected pulses, for example), but in many versions this information can be obtained by analyzing, filtering or otherwise processing pressure or other data from the restriction device (22) via one or more algorithms, which will be discussed in more detail below. The local unit (60), remote monitoring unit (170), and/or other device can implement these algorithms and continuously update the display (1900) with the results. The display (1900) can also include a cluster (1910) of recording controls to allow a user to control when pressure is recorded or logged to a file, and the location of such a log file can be shown in window (1924). In addition, an annotation function can be provided via control (1914). Annotation control (1914) may be used to annotate pressure readings shown on display (1900). As will be described in greater detail below, this annotation control (1914) may be substituted or supplemented with buttons (7022) of remote input device (7000). In some versions, the display (1900) can include pressure readings taken from prior visits (e.g., prior visits of the same patient, or from previous adjustments of the restriction device), and/or pressure readings of previous peristaltic events representing swallowing, heart rate, breathing rate, or virtually any other physiological parameter. The display (1900) also can include a patient's name or other identifying information, along with notes, lists of activities or guidelines for the patient, and so on.

Figure 13B:
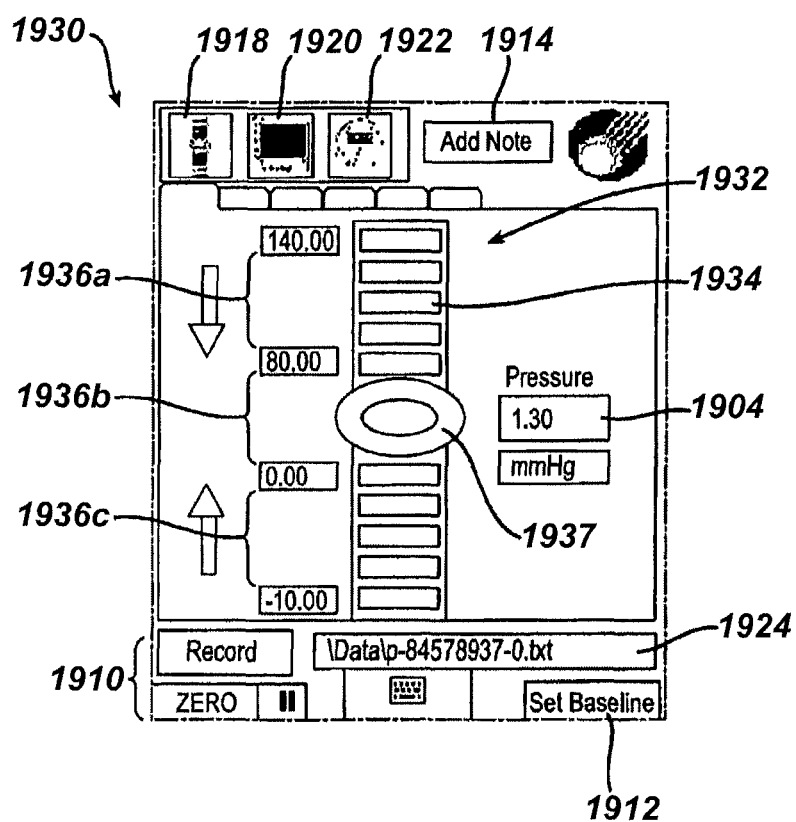
FIG. 13B shows an exemplary pressure meter display for a graphical user interface.

In FIG. 13A, the display (1900) has a menu (1916) that includes three graphics or icons (1918, 1920, 1922). Selection of each one of these icons (1918, 1920, 1922) can cause a different display screen to be presented. As shown in FIG. 13A, the second icon (1920) is selected and the graph (1902) of sensed pressure over time is shown. Selection of the first icon (1918) can lead to a display (1930) as shown in FIG. 13B, which indicates pressure via a meter (1932). In this version, the meter (1932) is vertical and linear, however, a wide variety of other orientations and shapes can be used, such as a horizontal meter, circular, and so on. The meter (1932) can include discrete indicators or bars (1934) which can be divided into one or more zones or ranges (1936A-C). As shown, three discrete pressure ranges (1936a-c) are provided with limits (in this example, 80 to 140 mmHg, 0 to 80 mmHg, and −10 to 0 mmHg), however any number of pressure ranges can be provided, and their size and endpoints can be adjustable. As one skilled in the art will understand, the ranges (1936A-C) can be set by a physician or other user and can vary from patient to patient.

In some versions, the pressure ranges (1936A-C) can correspond to conditions related to an implantable restriction device (22). For example, the highest range can indicate that the restriction device (22) is over-filled or over-tightened, the middle range can indicate an optimally filled or optimally tightened restriction device (22), and the lower range can indicate an under-filled or loose restriction device. In use, the pressure can be indicated by a marker (1937), which can represent current pressure, average pressure, or other metrics related to pressure. In some versions, the marker (1937) can move continuously along the meter (1932), while in other versions, the marker (1936) can move in a discrete fashion from bar (1934) to bar (1934). Display (1930) also can contain many of the same or similar interface elements as in display (1900) shown in FIG. 13A, such as a cluster (1910) of recording controls, a window (1924) showing the location of a log file, and/or an annotation control (1914).

Figure 13C:
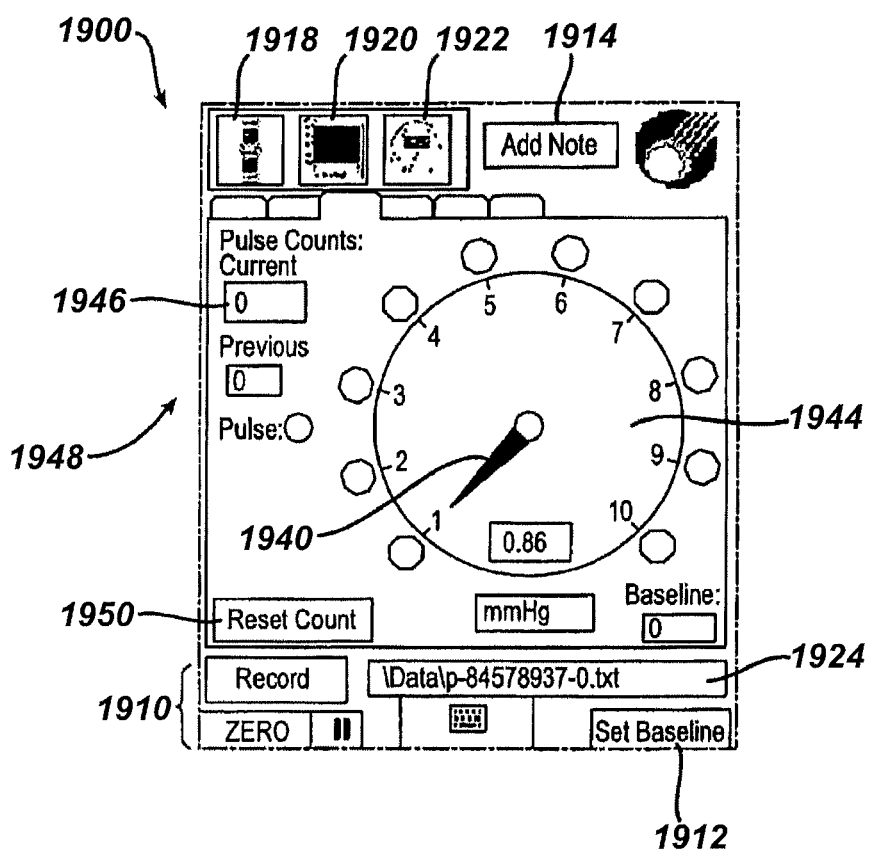
FIG. 13C shows an exemplary pulse counter display for a graphical user interface.

Returning to FIG. 13A, selection of the third icon (1922) can lead to a pulse count display (1940), as shown in FIG. 13C, for counting the number of pulses in a sequence of pulses. The sequence of pulses can represent a peristaltic event such as swallowing. The display (1940) can include a circular meter (1944) with numbering or indicators around its periphery. In use, an indicator needle (1932) can rotate within meter (1944) to provide an indication of the number of pulses detected in a sequence. Textual indicators (1946, 1948) can also be provided to indicate the number of pulses in the current or a past sequence of pulses. Control (1950) can reset the count.

Various other features and aspects that may be associated with displays (1900, 1930) shown in FIGS. 13A-13C are disclosed in U.S. Pub. No. 2008/0250340, entitled "GUI for an Implantable Restriction Device and a Data Logger," published Oct. 9, 2008, the disclosure of which is incorporated by reference herein. Various suitable ways in which the teachings herein and the teachings of U.S. Pub. No. 2008/0250340 may be combined and/or interchanged will be apparent to those of ordinary skill in the art.

In addition to providing a wide variety of displays based on or related to data or information from the restriction device (22), a graphical user interface provided through local unit (60) or some other component can provide or account for relevant data notated by the user. For instance, the user may wish to note the occurrence of physical events (e.g., eating, drinking, adding or removing fluid to and from the band, coughing, laughing, hiccupping, lying down, sitting up, standing up, burping, sneezing, vomiting, dry swallowing, etc.), such as in the form of a time stamp on a graph of pressure data, as described above. Such time stamps or other forms of indication may serve as a reminder to the same user at a later date (or notify another person or computer system evaluating the pressure data) that a certain physical event has occurred, and that the person or computer system evaluating the pressure data should take the occurrence of the physical event into account when evaluating the pressure data. For instance, it may be desirable to simply ignore pressure readings that are obtained shortly before, during, and or shortly after the occurrence of a physical event. To that end, FIGS. 14A-14C show variations of the displays (1900, 1930) shown in FIGS. 13A-13C.

Figure 14B:
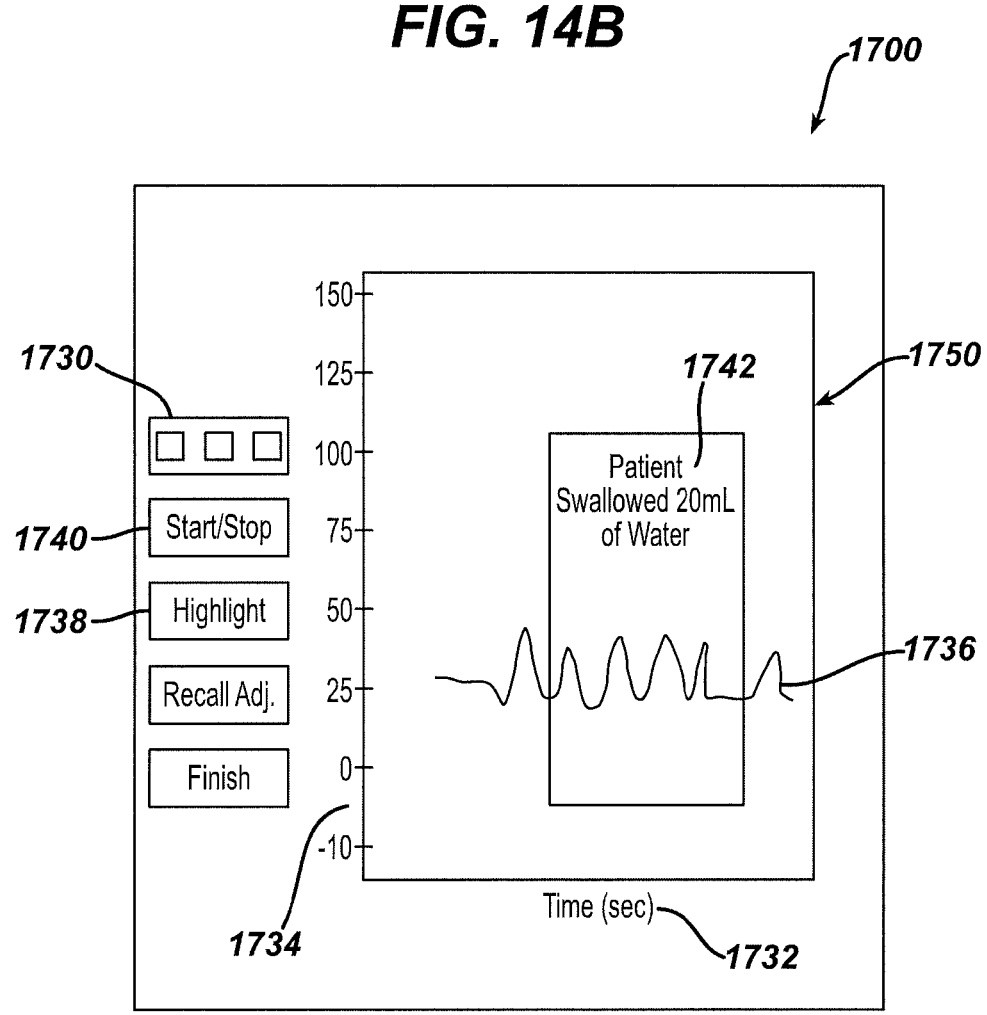
FIG. 14B shows an exemplary flagging wet swallow display for a graphical user interface.
Figure 14C:
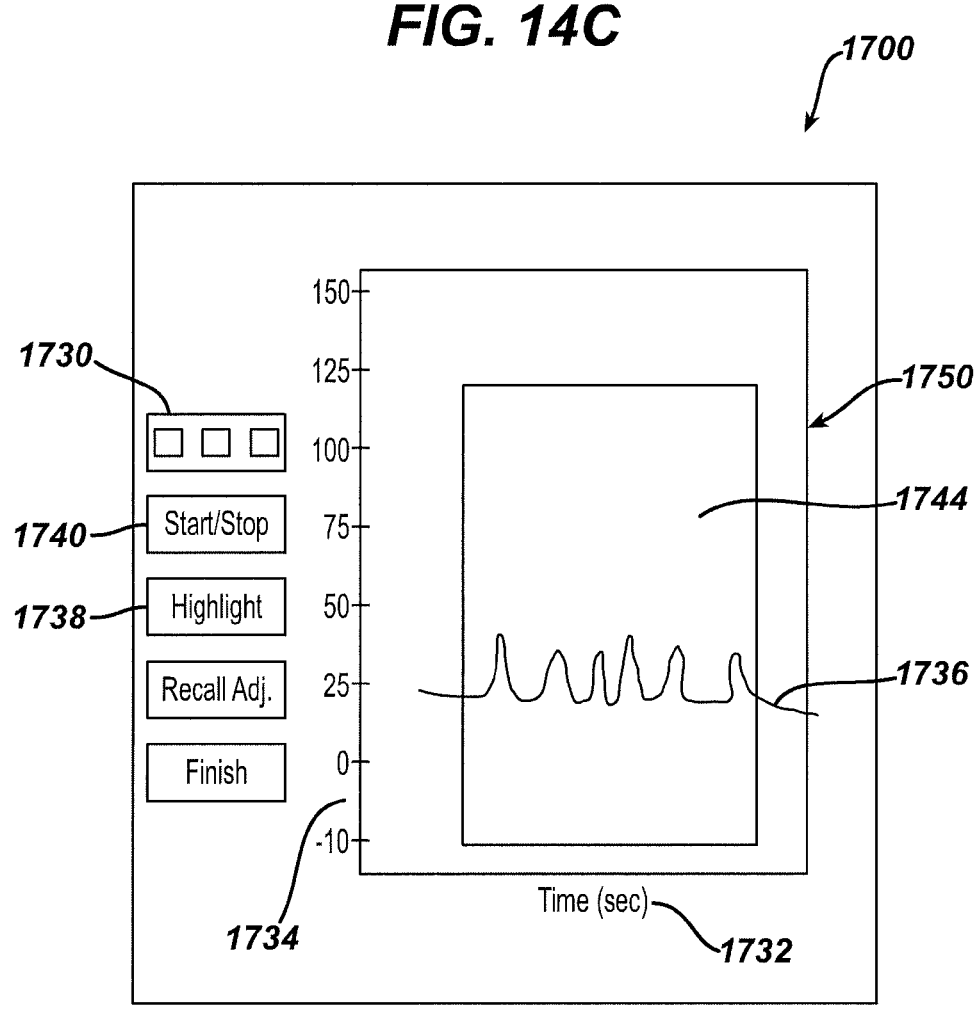
FIG. 14C shows an exemplary highlighting areas of interest display for a graphical user interface.

Like the displays (1900, 1930) shown in FIGS. 13A-13C, the displays (1700) shown in FIGS. 14A-14C may be provided through local unit (60). In addition, the display (1700) shown in FIGS. 14A-14C shows data similar to what is shown in the displays (1900, 1930) of FIGS. 13A-13C, except that display (1700) of FIGS. 14A-14C includes notations made by the user of remote input device (7000). For example, FIG. 14A shows that as saline is added to restriction device (22) or as the patient coughs, the pressure data (1736) may respond accordingly. A graph (1750) is shown with a horizontal axis (1732) representing time and a vertical axis (1734) representing a pressure reading. A portion (1710) of graph (1750) reflects the pressure readings as saline is added. Another portion (1720) of graph (1750) reflects the pressure readings where the patient coughs. Further, FIG. 14B shows a portion (1742) of graph (1750) where the pressure readings correspond to a wet swallow. Finally, FIG. 14C shows a portion (1744) of graph (1750) where the pressure readings correspond to a general area of interest. Thus, these visual indications (1710, 1720, 1742, 1744) may visually alert the person viewing display (1700) that a certain event occurred around a certain period of time, allowing the user to factor the occurrence of that event into their evaluation of the pressure readings from that same period of time.

The above described indications of saline being added (1710), the patient coughing (1720), the patient swallowing (1742), or some other occurrence of interest (1744) may be triggered through selected buttons (7022) of remote input device (7000), as will be described in greater detail below. Accordingly, and as shown in FIGS. 14A-C, it should be understood that the user may interact with the pressure graph (1750) by selectively activating buttons (7022) of remote input device (7000). It should also be understood that such interaction with the pressure graph (1750) may be effected through features that are provided directly on the graphical user interface of display (1700). For example, user can interact with a set of flagging events icons (1730) to annotate graph (1750) by adding a note (not shown) or by simply adding an icon (not shown). Flagging event icons (1730) may correspond with the same type of physical events described above with respect to buttons (7022) of remote input device (7000). In other words, each icon (1730) in the group of flagging event icons (1730) may be associated with a particular physical event (e.g., eating, drinking, adding or removing fluid to and from the band, coughing, laughing, hiccupping, lying down, sitting up, standing up, burping, sneezing, vomiting, dry swallowing, etc.) or particular group of events, such that the user may select an appropriate icon (1730) to mark or annotate a pressure reading that is substantially contemporaneous with the indicated physical event.

The user can start and stop recording pressure with a start/stop icon (1740). Additionally, user can highlight a portion of graph (1750) for later review with a highlight icon (1738). For example, the user may begin recording pressure data by pressing start/stop icon (1730), and if the patient coughs while recording pressure data, then user may press one of set of flagging events icons (1730) that may correspond to coughing. If, for example, an event occurs that is not accounted for with set of flagging events icons (1730), then the user may simply use highlight icon (1738) to highlight the area of interest, and upon obtaining necessary recordings, user may again press start/stop icon (1730) to end the pressure recording session.

Any or all of functions performed by set of flagging events icons (1730), highlight icon (1738), and/or start/stop icon (1740) may be incorporated into remote input device (7000) as discussed above. For instance, the same functionality of start/stop icon (1740) as described above may be provided by trigger (7102) of remote input device (7000). Similarly, the same functionality of flagging events icons (1730) and/or highlight icon (1738) may be provided by buttons (7022) of remote input device (7000). For instance, with remote input device (7000) being positioned over the patient as shown in FIG. 12, receiving pressure readings from coil (114), and transmitting the pressure readings to local unit (60), the user may activate a button (7022) on input device (7000) to annotate the pressure graph (1750) with an indication (1710) that saline is being added to band. Similarly, if the patient coughs while remote input device (7000) is receiving pressure readings from coil (114) and transmitting the pressure readings to local unit (60), the user may activate a button (7022) on input device (7000) to annotate the pressure graph (1750) with an indication (1720) that the patient has coughed. Buttons (7022) may likewise be used to annotate the pressure graph (1750) with an indication that the patient has swallowed water (1742) or that some other event has occurred (1744).

In the examples shown in FIGS. 14A-14C, visual indications (1710, 1720, 1742, 1744) are shown as simple boxes drawn in pressure graph (1750) corresponding with the time at which the noted events occurred. However, it should be understood that visual indications (1710, 1720, 1742, 1744) may take a variety of forms. By way of example only, indications (1710, 1720, 1742, 1744) may instead comprise graphical icons representing the noted physical event (e.g., an icon graphically representing a sneeze) or representing the group in which the noted physical event is placed. As another merely illustrative example, indications (1710, 1720, 1742, 1744) may include textual annotations positioned in pressure graph (1750) at locations corresponding with the time at which the noted physical event occurred. As yet another merely illustrative example, indications (1710, 1720, 1742, 1744) may be provided as a change in color of the line in graph (1750) representing pressure data (1736), a change in quality of the line in graph (1750) representing pressure data (1736) (e.g., broken or dotted line, faded line, etc.), or some other change in the line in graph (1750) representing pressure data (1736). Such changes in the line in graph (1750) representing pressure data (1736) may be located such that they correspond with the time at which the noted physical event occurred. Alternatively, the line in graph (1750) representing pressure data (1736) may simply be deleted or left blank during the time period at which the noted physical event occurred. For instance, one or more buttons (7022) may be used to omit certain areas of pressure data (1736) corresponding with a patient talking, coughing, etc.

As another merely illustrative example, one or more buttons (7022) may be used to mark a real-time pressure value (e.g., mark pressure data (1736) at the time pressure data (1736) is captured on the hardware), such as by adding a horizontal marker or other type of marker to pressure data (1736) at a desired time. For instance, when the pressure of fluid in adjustable band (28) is at a still or static state (e.g., while patient is being still/quiet and when fluid is not being added to or withdrawn from adjustable band (28), etc.), one or more buttons (7022) may be used to add a horizontal line in graph (1750) that corresponds with the present pressure level, and such a horizontal line may maintain its vertical position as time progresses. Such a horizontal line may thus be used as a baseline against which subsequent pressure data (1736) may be compared. Still other suitable ways in which noted physical events may be rendered or otherwise incorporated into display (1700) will be apparent to those of ordinary skill in the art in view of the teachings herein.

In some versions, particularly those in which remote input device (7000) communicates with local unit (60) wirelessly, remote input device (7000) and/or other components of the system may be configured to go into a "sleep" mode or "standby" mode after a certain period of time has elapsed without activity. For instance, such a mode may be triggered when neither buttons (7022, 7030) nor trigger (7012) has been actuated for a certain period of time. Remote input device (7000) and/or other components of the system may be configured to consume less power when a "sleep" mode or "standby" mode has been triggered due to such inactivity. In some such versions, remote input device (7000) and/or other components of the system may be configured to "wake up" from such a "sleep" mode or "standby" mode, and thus transition to a fully operating mode, as soon as either one or more buttons (7022, 7030) and/or trigger (7012) is/are actuated by the user. It should be understood that a user's actuation of one or more buttons (7022, 7030) and/or trigger (7012) may thus "wake up" wireless technology, other hardware, software, etc.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

It will also be readily apparent to those skilled in the art that examples described herein may have applicability to other types of devices (i.e., not just implantable bands per se). For instance, a syringe and needle fitted with a pressure sensing component may be used to adjust the pressure of fluid within a gastric balloon or other volume occupying device; the pressure of fluid within an infusion port; etc. Various other types of devices and systems with which the examples described herein may be used will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a sensor configured to detect parameter measurements associated with an implantable device;
   (b) a non-transitory storage device in communication with the sensor, wherein the non-transitory storage device is configured to record a plurality of data points associated with the parameter measurements from the sensor; and
   (c) a remotely positioned input device in communication with the storage device, wherein the remotely positioned input device is configured to transmit to the non-transitory storage device, in response to an action by a user, at least one preprogrammed signal corresponding to at least one of the received plurality of data points associated with the parameter measurements, wherein the remotely positioned input device comprises a housing operable to be held by a user during the operation of the remotely positioned input device, wherein the housing comprises at least one manually operable button, wherein the housing is shaped to be graspable by a user, wherein the remotely positioned input device is configured to relay parameter measurements from the sensor to the non-transitory storage device in real-time, wherein the manually operable buttons are configured to add annotations to the relayed parameter measurements in real-time as the parameter measurements are relayed.

2. The apparatus of claim 1, further comprising a start and stop trigger in communication with the sensor, wherein the start and stop trigger is configured to start and stop transmission of the plurality of data points associated with the parameter measurement by the sensor to the storage device.

3. The apparatus of claim 1, wherein the parameter measurement comprises a pressure measurement.

4. The apparatus of claim 3, wherein the pressure measurement corresponds to an intradevice pressure contained within an implantable device.

5. The apparatus of claim 1, further comprising a display configured to show the plurality of data points.

6. The apparatus of claim 5, wherein the display is further configured to show a representation of the at least one preprogrammed signal in conjunction with the plurality of data points.

7. The apparatus of claim 6, wherein the representation of the at least one preprogrammed signal is a graphical representation of a physical occurrence.

8. The apparatus of claim 5, wherein the remotely positioned input device is further configured to wirelessly communicate with the sensor.

9. The apparatus of claim 1, wherein the implantable device comprises a gastric band, wherein parameter measurements comprise pressure measurements associated with the gastric band, wherein the at least one preprogrammed signal is associated with activity by a patient associated with the gastric band.

10. An apparatus comprising:
    (a) a pressure sensor, wherein the pressure sensor is configured to sense pressure associated with an implantable restriction device;
    (b) an external antenna device configured to receive pressure data from the pressure sensor, wherein the external antenna device comprises a housing operable to be graspable by a user, wherein the housing defines an opening, wherein the housing comprises one or more user input features, wherein at least one of the one or more user input features on the external antenna device is operable to annotate the pressure data from the pressure sensor, wherein the one or more user input features are engageable by a user while grasping the housing through the opening;
    (c) a telemetry device contained within the housing, wherein the telemetry device is configured to communicate with the implantable restriction device; and
    (d) a display device in communication with the external antenna device, wherein the display device is configured to receive annotated pressure data from the external antenna device, wherein the display device is further configured to display at least a portion of the annotated pressure data, wherein the annotated pressure data comprises at least one annotation, wherein the at least one annotation relates to a patient condition event, wherein the annotations are added to the pressure data in real-time, wherein the annotations are added at time occurrences in the pressure data corresponding to the patient condition events.

11. The apparatus of claim 10, wherein the one or more user input features further comprises a trigger switch, wherein the trigger switch is configured to selectively activate a selected one of communication of pressure data from the pressure sensor to the external antenna device or communication of annotated pressure data from the external antenna device to the display device.

12. The apparatus of claim 10, wherein the display device is configured to display a pressure component of the annotated pressure data as a plot of pressure versus time.

13. The apparatus of claim 12, wherein the display device is further configured to display an annotation component of the annotated pressure data as the annotation in the plot of pressure versus time.

14. The apparatus of claim 13, wherein the annotation component comprises a graphical icon representing the occurrence of a physical event, wherein the graphical icon is positioned on the plot at a location corresponding with the time of the occurrence of the physical event.

15. The apparatus of claim 13, wherein the annotation component comprises a highlighting feature about the plot of pressure versus time, wherein the highlighting feature represents the occurrence of a physical event, wherein the highlighting feature is positioned on or near the plot at a location corresponding with the time of the occurrence of the physical event.

16. The apparatus of claim 13, wherein the annotation component comprises a textural representation of the occurrence of a physical event, wherein the textual representation is positioned on or near the plot at a location corresponding with the time of the occurrence of the physical event.

17. The apparatus of claim 10, wherein annotations associated with the one or more user input features relate to the occurrence of a physical event.

18. The apparatus of claim 10, further comprising an injection port associated with the implantable restriction device, wherein the pressure sensor is configured to sense the pressure of fluid in the injection port.

19. A method for recording a measurement with a remote input device in wireless communication with an implantable device, wherein the measurement is associated with the implantable device, wherein the remote input device comprises at least one manually operable control, wherein the remote input device is further in wireless communication with a local unit, the method comprising:

(a) holding the input device;
(b) initiating a measurement reading session by engaging the remote input device through the at least one manually operable control;
(c) recording a plurality of measurements associated with the implantable device, wherein the act of recording occurs at the local unit;
(d) making an annotation with the remote input device by sending a signal from the remote input device to the local unit, wherein the annotation is associated with at least one of the plurality of measurements, wherein the act of making an annotation with the remote input device occurs while holding the remote input device, wherein the act of making an annotation occurs by engaging the at least one manually operable control to send a signal to the local unit from the remote input device;
(e) storing the annotation at the local unit; and
(f) ending the session by engaging the remote input device through the at least one manually operable control.

20. The apparatus of claim 10, wherein the housing has a toroidal shape.

* * * * *